(12) United States Patent
Connor

(10) Patent No.: US 11,557,020 B2
(45) Date of Patent: Jan. 17, 2023

(54) EYE TRACKING METHOD AND APPARATUS

(71) Applicant: Sony Interactive Entertainment Inc., Tokyo (JP)

(72) Inventor: Patrick John Connor, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 206 days.

(21) Appl. No.: 16/970,487

(22) PCT Filed: Feb. 11, 2019

(86) PCT No.: PCT/GB2019/050357
§ 371 (c)(1),
(2) Date: Aug. 17, 2020

(87) PCT Pub. No.: WO2019/162645
PCT Pub. Date: Aug. 29, 2019

(65) Prior Publication Data
US 2020/0410644 A1    Dec. 31, 2020

(30) Foreign Application Priority Data

Feb. 23, 2018   (GB) .................................... 1802928

(51) Int. Cl.
*G06T 3/40*   (2006.01)
*G06V 40/18*   (2022.01)
*A61B 3/113*   (2006.01)

(52) U.S. Cl.
CPC .......... *G06T 3/4053* (2013.01); *G06V 40/193* (2022.01); *A61B 3/113* (2013.01)

(58) Field of Classification Search
CPC ..... G06T 3/4053; G06V 40/193; A61B 3/113; G02B 27/0093; G02B 27/017; G02B 2027/0181; G02B 2027/0198; G06F 3/013
See application file for complete search history.

(56) References Cited

U.S. PATENT DOCUMENTS 10,231,614 B2 *   3/2019   Krueger ................ A61B 5/1121
2013/0050645 A1 *   2/2013   Sato .......................... A61B 3/13
                                                                 351/206

(Continued)

FOREIGN PATENT DOCUMENTS

CN    106233349 A   * 12/2016   ......... G08B 21/0263
GB    2548151 A   9/2017

(Continued)

OTHER PUBLICATIONS

International Search Report and Written Opinion for corresponding PCT Application No. PCT/GB2019/050357, 13 pages, dated May 8, 2019.

(Continued)

*Primary Examiner* — Ryan R Yang
(74) *Attorney, Agent, or Firm* — Matthew B. Dernier, Esq.

(57) ABSTRACT

An eye tracking system for tracking one or more of a user's eyes includes an closed-eye detector operable to detect when a user has closed one or more of their eyes, an eye tracker operable to detect an eye orientation in dependence upon a measured deformation of an eyelid corresponding to the an eye that has been detected to be shut, and an image renderer operable to render a foveated image for display in response to the detected eye orientation.

14 Claims, 10 Drawing Sheets

(56) References Cited

U.S. PATENT DOCUMENTS

| | | | |
|---|---|---|---|
| 2017/0123526 A1 | 5/2017 | Trail | |
| 2017/0177075 A1* | 6/2017 | Zhang | .................. G06V 40/19 |
| 2017/0178408 A1 | 6/2017 | Bavor, Jr. | |
| 2017/0285735 A1 | 10/2017 | Young | |

FOREIGN PATENT DOCUMENTS

| | | | | |
|---|---|---|---|---|
| JP | 2005205024 A | 8/2005 | | |
| JP | 2016137155 A | 8/2016 | | |
| WO | WO2015050250 A1 * | 4/2015 | ............ | G06T 5/005 |
| WO | WO2017054279 A1 * | 4/2017 | ............ | G08B 21/06 |
| WO | 2017177187 A1 | 10/2017 | | |

OTHER PUBLICATIONS

Combined Search and Examination Report for corresponding GB Application No. GB1802928.0, 5 pages, dated Aug. 8, 2018.

\* cited by examiner

LEFT             RIGHT

EYE TRACKING METHOD AND APPARATUS

BACKGROUND

This disclosure relates to an eye tracking method and apparatus, for example for use with a head-mountable display unit (HMD).

SUMMARY

HMDs have become increasingly common in recent years as display devices for the delivery of entertainment content such as movies, games, and other virtual reality (VR) experiences. In these use cases it is common for content to be provided to a user in such a manner so as to provide an immersive experience, causing the user to believe that they are within the environment that they are viewing. This may be achieved by rendering the display using a viewpoint that is responsive to a user's head motion, for example.

Examples of limitations with such content are those of the high bandwidth and processing requirements that are desired for providing high-quality content. For example, these factors may be required to generate an image that is both responsive to user inputs and of a high enough image quality so as to appear realistic to the viewer. If either of these features is not provided by generated content (for example, low responsiveness/high latency and/or low image quality) then a user may find it difficult to suspend their disbelief and become fully immersed in the content.

One general approach that is considered is that of optimising the use of the available bandwidth. By using the available bandwidth more efficiently, it is possible that higher quality image data may be provided to a user without any hardware modifications, and therefore the sense of immersion may be increased.

One example of such a method is that of foveal rendering techniques. Such techniques provide high-resolution image areas where the user is focussed, and lower-resolution image areas elsewhere. The area of the display upon which the viewer is focussed may be identified either by prediction (such as expecting a user to view certain displayed objects) or by gaze tracking, for example. While the latter of these may be more accurate, it may suffer from inaccuracies due to a user closing their eyes (for example, during a blink) and moving their eyes while they are closed—this may cause incorrect areas of the generated images to be higher-resolution, leaving the user viewing lower-resolution content. This can cause a loss of the sense of immersion for a user, thus reducing the enjoyment of the VR experience by a user.

Several solutions have been proposed to mitigate the problems arising in this case. For example, a 'last known gaze position' may be used, as this may be a useful approximation of the user's eye position after a blink. Alternatively, the higher-resolution area may be dynamically expanded so as to anticipate all possible movements of the user's eyes during the period in which the user's eyes are closed. A third method is that of defining a default area in the centre of the displayed image that is selected as the area of higher resolution upon closing of the user's eyes.

Of course, the use of an accurate system and method for tracking a user's eyes extends beyond that of foveal rendering; eye tracking data may be utilised for a number of other applications, such as for hands-free inputs to an entertainment system or the like. The discussion of the applications of such a system and method in the context of foveal rendering is presented merely as an example use case.

It is in the context of the above problems that the present invention is provided.

This disclosure supports the appended claims.

BRIEF DESCRIPTION OF THE DRAWING

Embodiments of the disclosure will now be described with reference to the accompanying drawings, in which.

DETAILED DESCRIPTION OF THE EMBODIMENTS

While the present disclosure frames the system and method in the context of an HMD, it would be understood by the skilled person that the use of an HMD is not essential and therefore the scope of the present disclosure should not be limited to such embodiments. Whilst the use of cameras located near to the user's eyes may be desirable in order to provide a suitable degree of accuracy, as noted above eye tracking may be used as an input to an entertainment system or the like which would not generally comprise a head-mountable component. It is therefore apparent that a display is not necessary, and as such an apparatus may be provided that does not incorporate a display. For instance, a head-mountable unit may be provided that comprises cameras for eye tracking, but does not comprise a display unit.

As noted above, embodiments of the present disclosure are suitable for use with an HMD; to that effect, the operation and structure of a general HMD system is provided below.

A head mountable display may have a frame to be mounted onto an viewer's head, the frame defining one or two eye display positions which, in use, are positioned in front of a respective eye of the viewer and a respective display element is mounted with respect to each of the eye display positions, the display element providing a virtual image of a video display of a video signal from a video signal source to that eye of the viewer. In other examples, the display is not a head-mountable display. In some embodiments, the display (whether head mountable or not) may be referred to as an immersive display, in that in normal use it fills at least a threshold angular range (for example, at least 40°) of the field of view of the user. Examples include multiple projector displays, wrap-around (curved) displays and the like.

Figure 1:
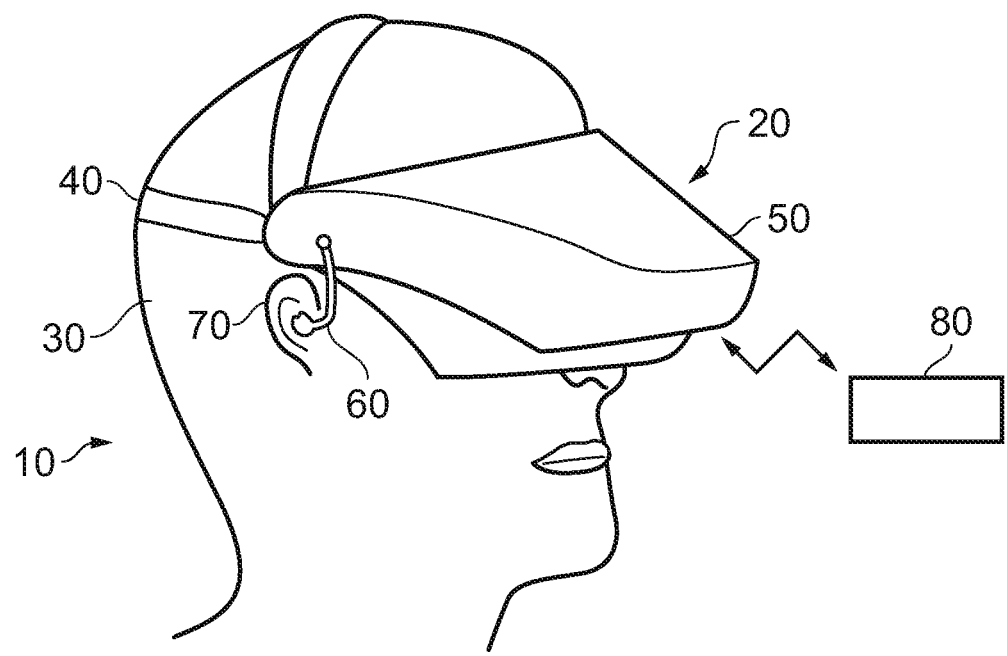
FIG. 1 schematically illustrates an HMD worn by a user.

Referring now to FIG. 1, a user 10 is wearing an HMD 20 on the user's head 30. The HMD comprises a frame 40, in this example formed of a rear strap and a top strap, and a display portion 50.

The HMD of FIG. 1 completely obscures the user's view of the surrounding environment. All that the user can see is the pair of images displayed within the HMD.

The HMD has associated headphone earpieces 60 which fit into the user's left and right ears 70. The earpieces 60 replay an audio signal provided from an external source, which may be the same as the video signal source which provides the video signal for display to the user's eyes.

In operation, a video signal is provided for display by the HMD. This could be provided by an external video signal source 80 such as a video games machine or data processing apparatus (such as a personal computer), in which case the signals could be transmitted to the HMD by a wired or a wireless connection. Examples of suitable wireless connections include Bluetooth® connections. Audio signals for the earpieces 60 can be carried by the same connection. Similarly, any control signals passed from the HMD to the video (audio) signal source may be carried by the same connection.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other examples, the user's view of the external environment may not in fact be entirely obscured; the displayed images could be arranged so as to be superposed (from the user's point of view) over the external environment. An example of such an arrangement will be described below with reference to FIG. 4.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160. The way in which the display element and the optical element(s) cooperate to provide a display to the user will be described with reference to FIG. 3.

Figure 2:
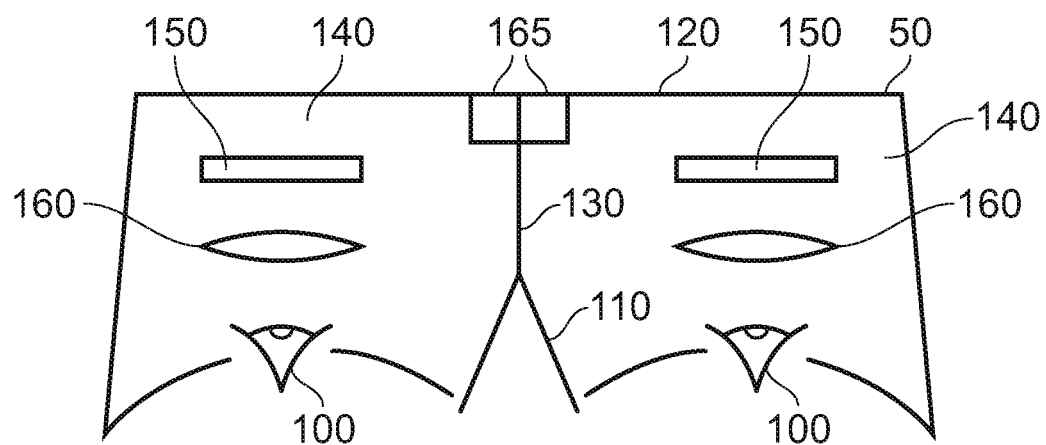
FIG. 2 is a schematic plan view of an HMD.

FIG. 2 also shows a pair of inward-facing cameras 165; these may be RGB, IR or depth cameras, for example, or any suitable alternative for performing the methods described within the present disclosure.

Figure 3:
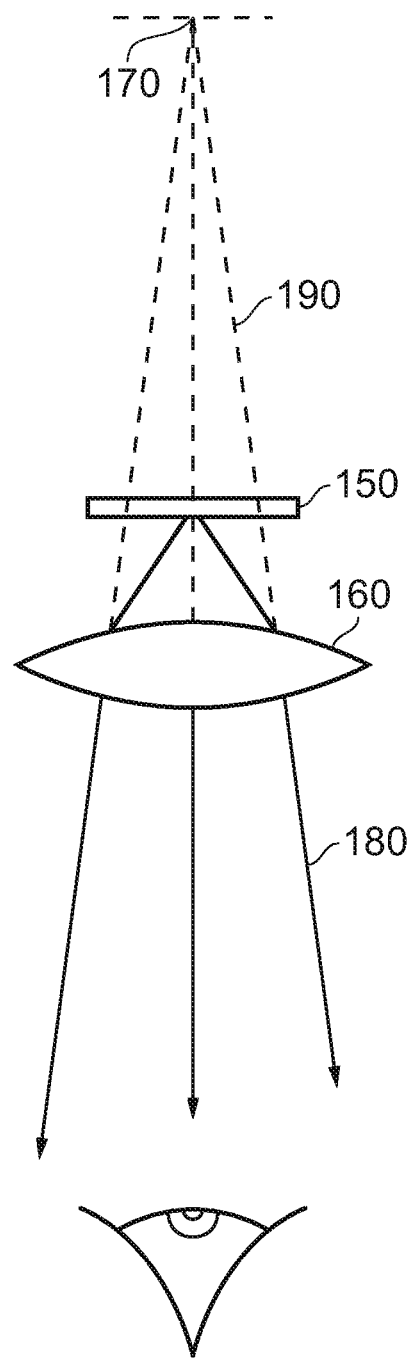
FIG. 3 schematically illustrates the formation of a virtual image by an HMD.

Referring to FIG. 3, the display element 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several metres. In FIG. 3, solid lines (such as the line 180) are used to denote real optical rays, whereas broken lines (such as the line 190) are used to denote virtual rays.

Figure 4:
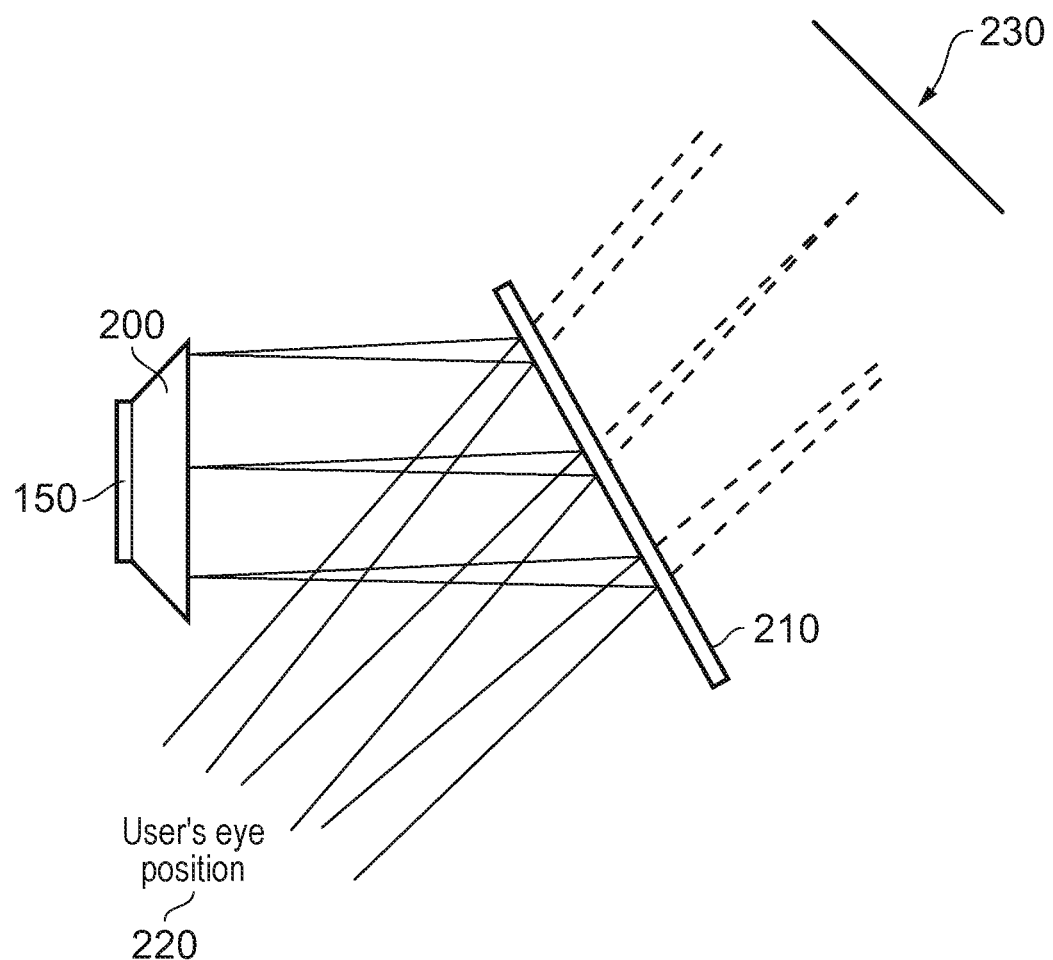
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
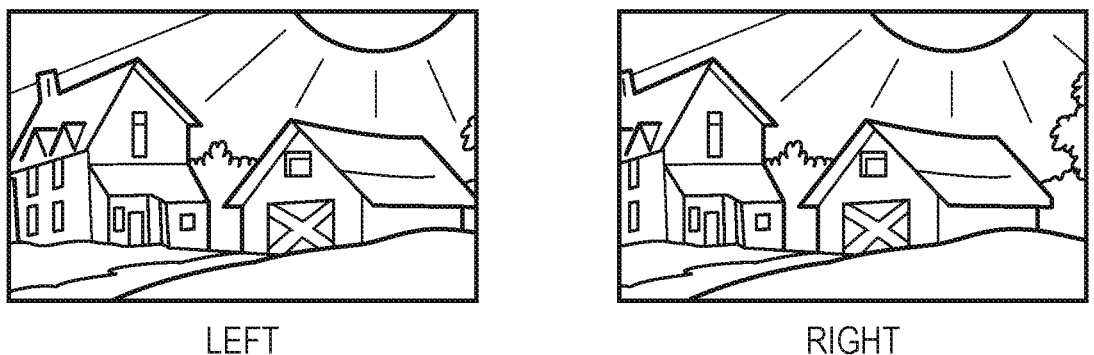
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 (and those in FIG. 15 to be described below) could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint need to track movements with respect to a real or virtual space in which the user is located.

This tracking is carried out by detecting motion of the HMD and varying the apparent viewpoint of the displayed images so that the apparent viewpoint tracks the motion.

Figure 6:
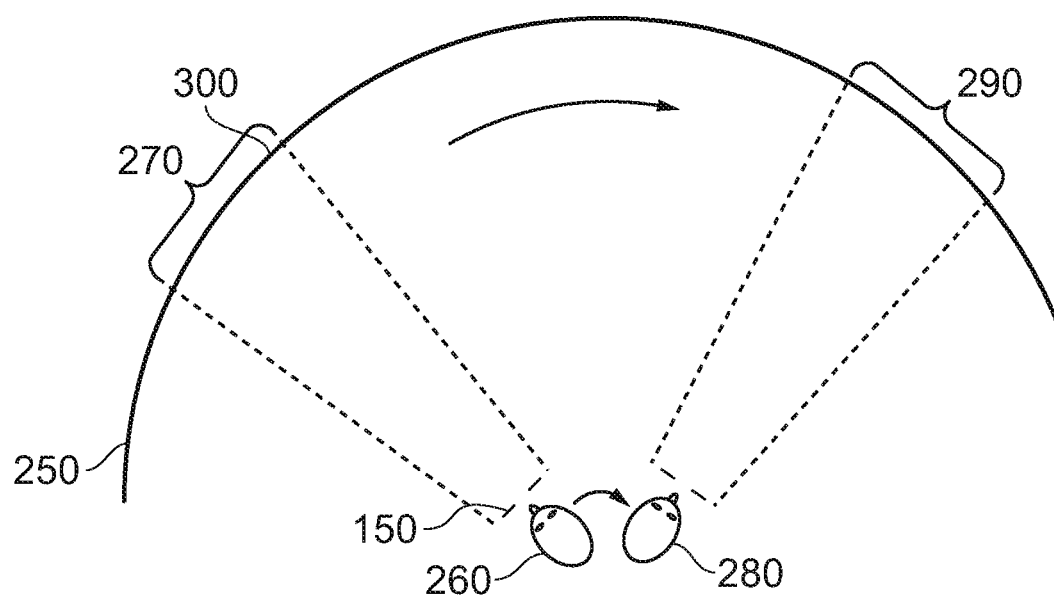
FIG. 6 schematically illustrates a change of view of user of an HMD.

FIG. 6 schematically illustrates the effect of a user head movement in a VR or AR system.

Referring to FIG. 6, a virtual environment is represented by a (virtual) spherical shell 250 around a user. Because of the need to represent this arrangement on a two-dimensional paper drawing, the shell is represented by a part of a circle, at a distance from the user equivalent to the separation of the displayed virtual image from the user. A user is initially at a first position 260 and is directed towards a portion 270 of the virtual environment. It is this portion 270 which is represented in the images displayed on the display elements 150 of the user's HMD.

Consider the situation in which the user then moves his head to a new position and/or orientation 280. In order to maintain the correct sense of the virtual reality or augmented reality display, the displayed portion of the virtual environment also moves so that, at the end of the movement, a new portion 290 is displayed by the HMD.

So, in this arrangement, the apparent viewpoint within the virtual environment moves with the head movement. If the head rotates to the right side, for example, as shown in FIG. 6, the apparent viewpoint also moves to the right from the user's point of view. If the situation is considered from the aspect of a displayed object, such as a displayed object 300, this will effectively move in the opposite direction to the head movement. So, if the head movement is to the right, the apparent viewpoint moves to the right but an object such as the displayed object 300 which is stationary in the virtual environment will move towards the left of the displayed image and eventually will disappear off the left-hand side of the displayed image, for the simple reason that the displayed portion of the virtual environment has moved to the right whereas the displayed object 300 has not moved in the virtual environment. Similar considerations apply to the up-down component of any motion.

Figure 7A:
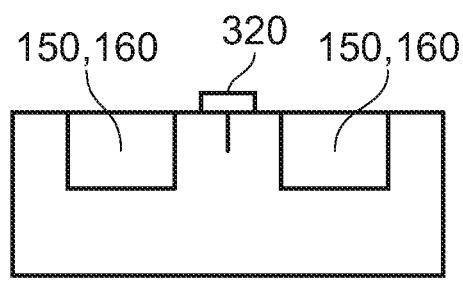
FIGS. 7a and 7b schematically illustrate HMDs with motion sensing.
Figure 7B:
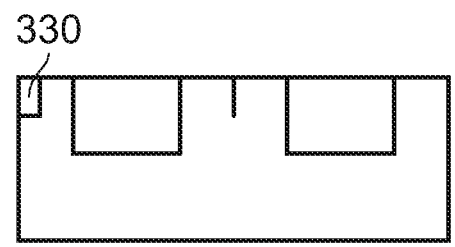

FIGS. 7a and 7b schematically illustrated HMDs with motion sensing. The two drawings are in a similar format to that shown in FIG. 2. That is to say, the drawings are schematic plan views of an HMD, in which the display element 150 and optical elements 160 are represented by a simple box shape. Many features of FIG. 2 are not shown, for clarity of the diagrams. Both drawings show examples of HMDs with a motion detector for detecting motion of the observer's head.

In FIG. 7a, a forward-facing camera 320 is provided on the front of the HMD. This does not necessarily provide images for display to the user (although it could do so in an augmented reality arrangement). Instead, its primary purpose in the present embodiments is to allow motion sensing. A technique for using images captured by the camera 320 for motion sensing will be described below in connection with FIG. 8. In these arrangements, the motion detector comprises a camera mounted so as to move with the frame; and an image comparator operable to compare successive images captured by the camera so as to detect inter-image motion.

FIG. 7b makes use of a hardware motion detector 330. This can be mounted anywhere within or on the HMD. Examples of suitable hardware motion detectors are piezoelectric accelerometers or optical fibre gyroscopes. It will of course be appreciated that both hardware motion detection and camera-based motion detection can be used in the same device, in which case one sensing arrangement could be used as a backup when the other one is unavailable, or one sensing arrangement (such as the camera) could provide data for changing the apparent viewpoint of the displayed images, whereas the other (such as an accelerometer) could provide data for image stabilisation.

Figure 8:
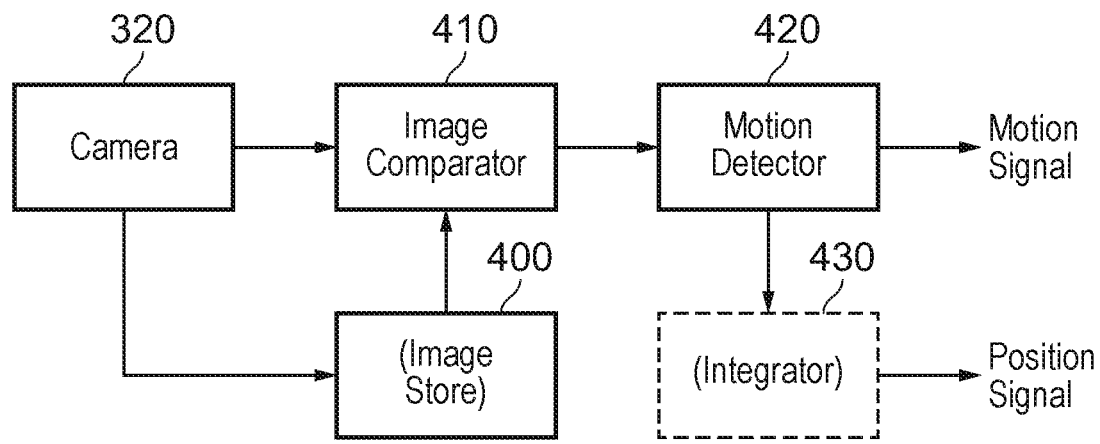
FIG. 8 schematically illustrates a position sensor based on optical flow detection.

FIG. 8 schematically illustrates one example of motion detection using the camera 320 of FIG. 7a.

The camera 320 is a video camera, capturing images at an image capture rate of, for example, 25 images per second. As each image is captured, it is passed to an image store 400 for storage and is also compared, by an image comparator 410, with a preceding image retrieved from the image store. The comparison uses known block matching techniques (so-called "optical flow" detection) to establish whether substantially the whole image captured by the camera 320 has moved since the time at which the preceding image was captured. Localised motion might indicate moving objects within the field of view of the camera 320, but global motion of substantially the whole image would tend to indicate motion of the camera rather than of individual features in the captured scene, and in the present case because the camera is mounted on the HMD, motion of the camera corresponds to motion of the HMD and in turn to motion of the user's head.

The displacement between one image and the next, as detected by the image comparator 410, is converted to a signal indicative of motion by a motion detector 420. If required, the motion signal is converted by to a position signal by an integrator 430.

As mentioned above, as an alternative to, or in addition to, the detection of motion by detecting inter-image motion between images captured by a video camera associated with the HMD, the HMD can detect head motion using a mechanical or solid state detector 330 such as an accelerometer. This can in fact give a faster response in respect of the indication of motion, given that the response time of the video-based system is at best the reciprocal of the image capture rate. In some instances, therefore, the detector 330 can be better suited for use with higher frequency motion detection. However, in other instances, for example if a high image rate camera is used (such as a 200 Hz capture rate camera), a camera-based system may be more appropriate. In terms of FIG. 8, the detector 330 could take the place of the camera 320, the image store 400 and the comparator 410, so as to provide an input directly to the motion detector 420. Or the detector 330 could take the place of the motion detector 420 as well, directly providing an output signal indicative of physical motion.

Other position or motion detecting techniques are of course possible. For example, a mechanical arrangement by which the HMD is linked by a moveable pantograph arm to a fixed point (for example, on a data processing device or on a piece of furniture) may be used, with position and orientation sensors detecting changes in the deflection of the pantograph arm. In other embodiments, a system of one or more transmitters and receivers, mounted on the HMD and on a fixed point, can be used to allow detection of the position and orientation of the HMD by triangulation techniques. For example, the HMD could carry one or more directional transmitters, and an array of receivers associated with known or fixed points could detect the relative signals from the one or more transmitters. Or the transmitters could be fixed and the receivers could be on the HMD. Examples of transmitters and receivers include infra-red transducers, ultrasonic transducers and radio frequency transducers. The radio frequency transducers could have a dual purpose, in that they could also form part of a radio frequency data link to and/or from the HMD, such as a Bluetooth® link.

Figure 9:
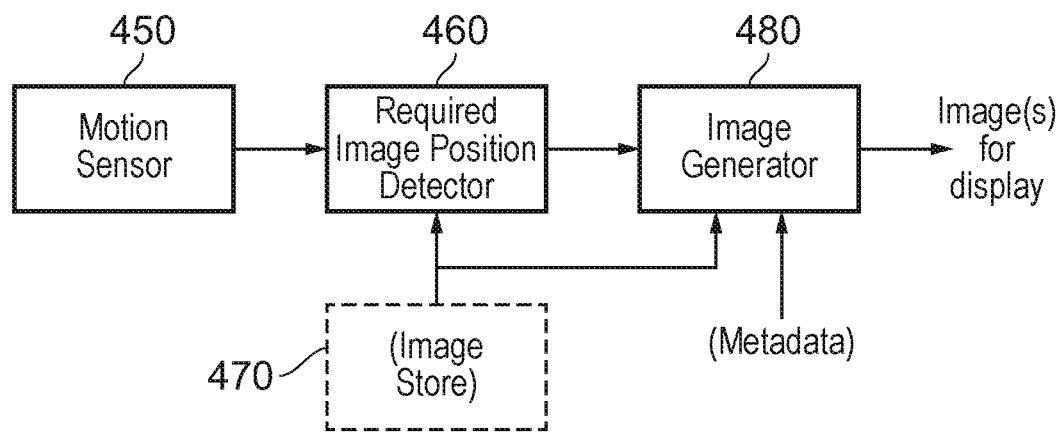
FIG. 9 schematically illustrates the generation of images in response to HMD position or motion detection.

FIG. 9 schematically illustrates image processing carried out in response to a detected position or change in position of the HMD.

As mentioned above in connection with FIG. 6, in some applications such as virtual reality and augmented reality arrangements, the apparent viewpoint of the video being displayed to the user of the HMD is changed in response to a change in actual position or orientation of the user's head.

With reference to FIG. 9, this is achieved by a motion sensor 450 (such as the arrangement of FIG. 8 and/or the motion detector 330 of FIG. 7b) supplying data indicative of motion and/or current position to a required image position detector 460, which translates the actual position of the HMD into data defining the required image for display. An image generator 480 accesses image data stored in an image store 470 if required, and generates the required images from the appropriate viewpoint for display by the HMD. The external video signal source can provide the functionality of the image generator 480 and act as a controller to compensate for the lower frequency component of motion of the observer's head by changing the viewpoint of the displayed image so as to move the displayed image in the opposite direction to that of the detected motion so as to change the apparent viewpoint of the observer in the direction of the detected motion.

The image generator 480 may act on the basis of metadata such as so-called view matrix data, in a manner to be described below.

Figure 10A:
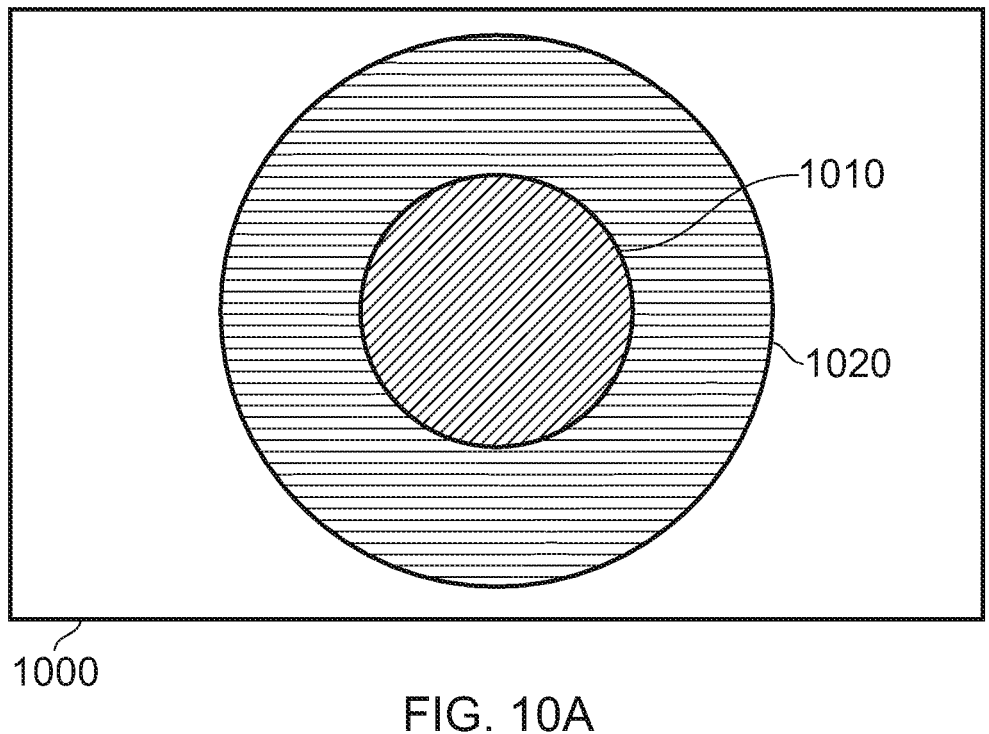
FIGS. 10A and 10B schematically illustrate foveal rendering regions.
Figure 10B:
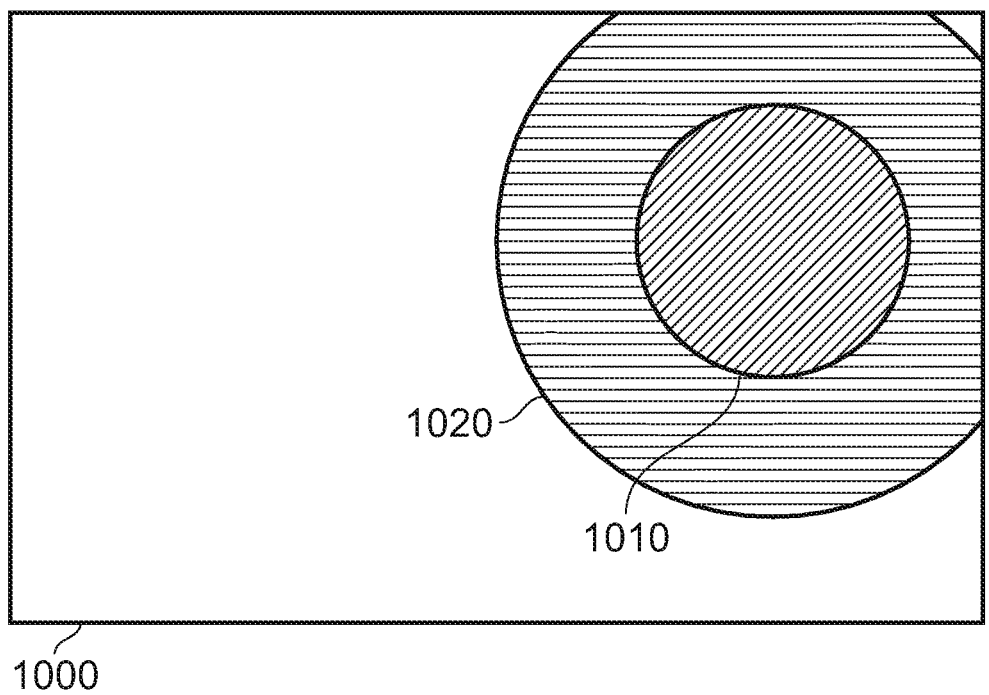

FIGS. 10A and 10B schematically illustrates an example of a foveal rendering technique as applied to an image.

FIG. 10A shows a display 1000 with an overlaid graphic representing a division of the display into separate regions. A first region 1010 corresponds to a central focal area which is expected to surround the user's point of focus on the display, while a second region 1020 corresponds to a surrounding area about the first region 1010. In a foveal rendering application, it would be expected that the highest image quality would be provided in the first region 1010, with lower-quality content being provided in the second region 1020 and still-lower-quality content being provided for all areas of the display 1000 that do not correspond to either of the first and second regions.

In some embodiments, the first region 1010 comprises the highest-resolution content, the second region 1020 comprises content with 80% of this resolution, and elsewhere content with 50% of this resolution is rendered. Of course, these numbers are entirely exemplary and may be selected freely by the person skilled in the art to use values that are suitable for the specific application.

While the regions 1010 and 1020 are shown as being circular, this is not essential in the present disclosure. The regions may take any suitable shape, such as providing rectangular or square regions, and indeed the two regions 1010 and 1020 may be different shapes to each other. Such shapes also need not be regular polygons, although it may simplify the implementation of the foveal rendering if regular polygons are used.

In some arrangements it may be assumed that the central area of the display is always the focal area, and therefore the first region 1010 is always in the centre of the display; however, these arrangements may be unsuitable in the case that a user views areas of the display other than the centre. To that end, gaze tracking (or other methods) may be implemented so as to identify where on the display 1000 the user is focused.

FIG. 10B shows a second view of the same display 1000 in which it is determined that the user's gaze direction has changed to look towards the top right corner of the display 1000. In this Figure it is apparent that the second region 1020 intersects the edge of the display 1000; in this case, a modified shape is used for the second region 1020.

One problem that may occur in foveal rendering arrangements is that of when a user's gaze position changes, but the regions 1010 and 1020 of FIGS. 10A and 10B do not reflect this. This may lead to the area that the user is focussing on being rendered at a lower resolution than would be desirable, and therefore a lower-quality viewing experience is provided to the viewer.

For example, if the user were viewing the top-right of the display 1000 and the foveal rendering shown in FIG. 10A were used for generating an image for display, then the user would be viewing mostly image content at the lowest resolution as the highest-resolution content would be in the centre of the display 1000 instead.

A source of these problems may be a loss of eye tracking information, for example when a user blinks or otherwise closes their eyes. During a blink, the user's eye may still be moving and therefore the point of focus on the display at the end of a blink may be different to that at the start of the blink. Once the user's blink has ended, they may therefore be provided with a displayed image that does not correspond to their current gaze direction and as a result their viewing experience may suffer.

While existing arrangements have sought to alleviate these problems, there are numerous drawbacks associated with the techniques implemented. For example, the foveal rendering technique may be suspended in the time immediately following a blink so as to avoid an incorrect region of high resolution being generated; however, this increases the rendering burden upon the image generating apparatus as a whole image must be generated at the highest resolution instead.

It can therefore be considered advantageous to perform eye tracking even while the user's eyes are closed.

Figure 11A:
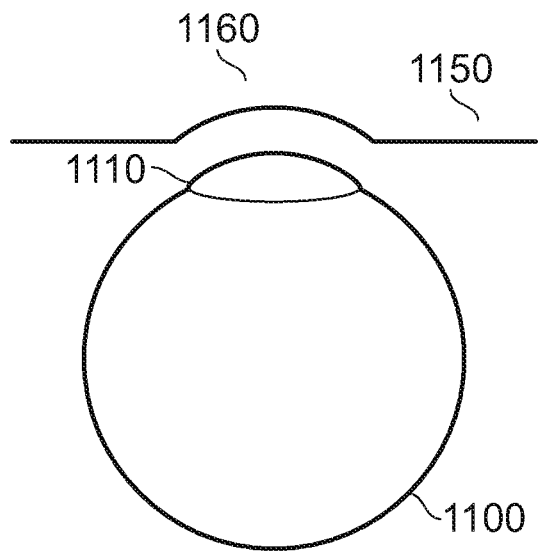
FIGS. 11A and 11B schematically illustrate eye motion.
Figure 11B:
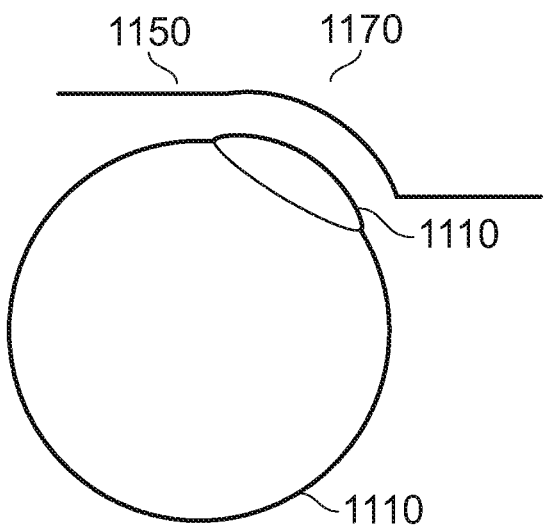

FIGS. 11A and 11B schematically illustrate an eye 1100 in two respective orientations, with the eyelid 1150 showing respective deformations 1160 and 1170.

In FIG. 11A, the user is looking in a substantially forwards direction. The cornea 1110 protrudes from the surface of the eye 1100, giving it a non-spherical surface. As a result of this, the cornea causes a deformation 1160 of the eyelid 1150 that is in an approximately central area of the eyelid 1150. By measuring this deformation 1160, it is possible to deduce the location of the cornea 1110 and, by extension, the position/orientation of the eye 1100. Using this information, the portion of the display that would be viewed by the user if the eye were not shut can be identified and the appropriate image rendering may be implemented.

In FIG. 11B, the user's eye 1100 has changed orientation so as to be looking towards the right of a display in front of the user. The change in orientation of the user's eye 1100, and therefore the change in position of the cornea 1110, causes a different deformation 1170 that is located in a different area and has a different profile to the deformation 1160 that is illustrated in FIG. 11A. It may therefore be possible to identify the location of the cornea 1110 from either the location of the deformation 1170, from the shape of the deformation 1170, or from a combination of the two.

Numerous methods may be used to determine the location and profile of deformations of the user's eyelids, several of which are discussed below. This detection may be performed for one or both of the user's eyes, as is appropriate for the application. In some embodiments, the detection may be performed for a single eye and a predictive model and/or information about the displayed image may be used to predict the orientation of the user's other eye.

In some embodiments, this detection is performed using a depth camera. An example of such a camera is a stereoscopic camera that is operable to capture a pair of images of the user's eyelid, and compare a disparity between the captured images in order to determine the depth of the features within the captured image.

Alternatively, or in addition, an RGB camera may be used to capture images of the user's eyelid that can be used to determine this information. It may be advantageous to use high-speed cameras (for example, 100 frames per second or greater) in order to ensure that a sufficient number of images are captured during each blink or other period of eye closure by a user.

The deformation of the user's eyelid caused by the cornea may be small; the thickness of the cornea is of the order of half a millimetre for most people. While a suitably high-resolution camera or the like would be able to detect such a deformation, such an arrangement may be prohibitive in terms of complexity or cost. It may therefore be advantageous to modify the described arrangement in other ways in order to improve the precision with which the deformation may be detected.

Figure 12:
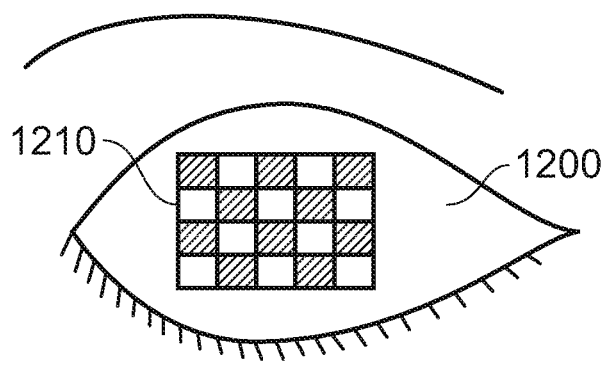
FIG. 12 schematically illustrates a pattern applied to a user's eyelid.

FIG. 12 schematically illustrates a method by which the precision of the detection may be improved. In FIG. 12, a user's eyelid 1200 is provided with a pattern 1210 that may be imaged by a camera performing the eye tracking. The provision of such a pattern may be beneficial in a number of embodiments as it may be used as an indication of a target area for performing a detection of the user's cornea, and the deformations of the eyelid may be exaggerated by the pattern.

In some embodiments, the pattern may be physically applied to the user's eyelid; for example, make-up, pens, stickers or temporary tattoos may be used to apply a pattern to the user's eyelids. In some examples, the patterns applied may be invisible to the human eye and instead are only visible by IR cameras or the like. This may encourage use of the patterns, as they would not be visible to other people when not using the eye-tracking arrangement and therefore the patterns may not need to be applied and then removed with each use.

Alternatively, or in addition, such a pattern may be projected onto the user's eyelid, for example using an arrangement for generating structured light. This projection may be performed in response to a detection of the user's eyes closing, in some embodiments. Alternatively, or in addition, a light frequency outside of the visible spectrum may be used such that the projection may optionally be performed at all times without interfering with the user's vision. Of course, the detectors provided in these arrangements must be capable of detecting the light frequency that is selected for projecting the pattern.

In FIG. 12, the pattern provided on the user's eyelid 1200 is a chequerboard pattern 1210 with squares of alternating light and dark colours (such as white and black). The shape of the pattern may of course be modified to reflect the fact that it is not applied to a planar surface; for example, a mapping could be used so as to give the appearance of a flat pattern to a camera or the like that is used to detect the pattern.

Of course, the use of a chequerboard pattern in FIG. 12 is entirely exemplary; any suitable pattern may be used. For example, patterns with a higher level of detail may be useful in enabling a more precise measurement of a deformation of the user's eyelid. Patterns need not be self-repeating, as in the chequerboard example, and may instead be a non-repeating pattern such as an AR marker or the like. It may also be the case that patterns with a high contrast level between colours used (or a single colour and the user's skin tone) is advantageous in the detection process.

Figure 13:
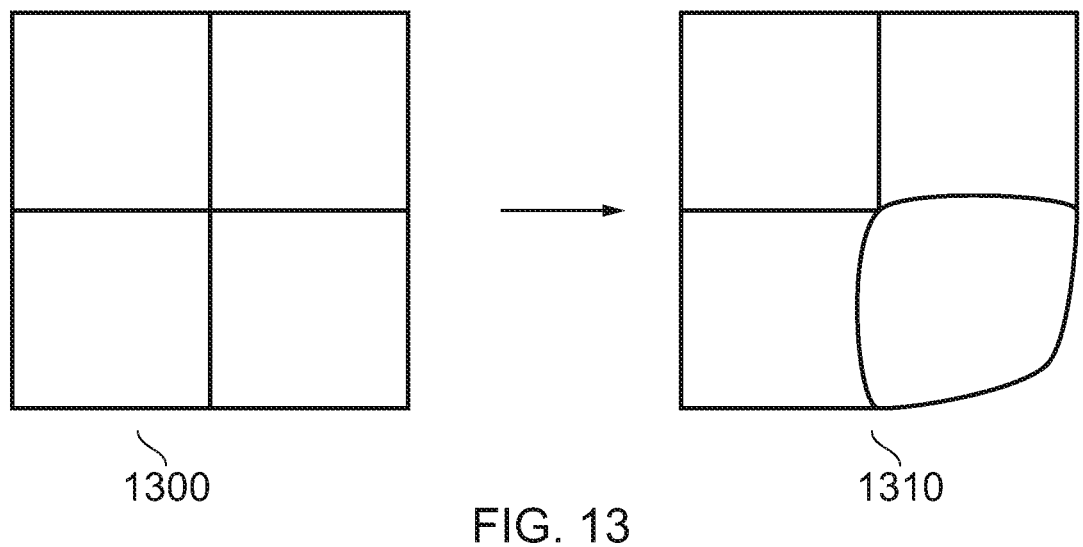
FIG. 13 schematically illustrates the deformation of a pattern applied to a user's eyelid.

FIG. 13 schematically illustrates an example of the deformation of a simple pattern in response to a motion of the user's eye.

The pattern 1300 is shown as a square, with internal lines dividing it into four equal portions. In practice, the equal portions may be filled with different colours in order to distinguish the different portions from one another more readily.

The pattern 1310 is a deformed version of the pattern 1300; this deformation is an example of how the pattern may appear if the user were to move their eye such that the cornea, and therefore deformation, were to be in the lower right-hand corner of the pattern 1300. Several of the lines of the pattern 1300 that were initially straight now appear curved in the pattern 1310, with the degree of curvature and/or the length of the portion of the lines that now appear curved being indicative of the deformation and therefore position of the cornea. A mapping may be provided that is used by a processing device in order to relate the amount/location of deformation to the position of the cornea, for example.

Therefore the location of the user's cornea may be determined in dependence upon the detected deformation of the pattern applied to the user's eyelid.

Figure 14:
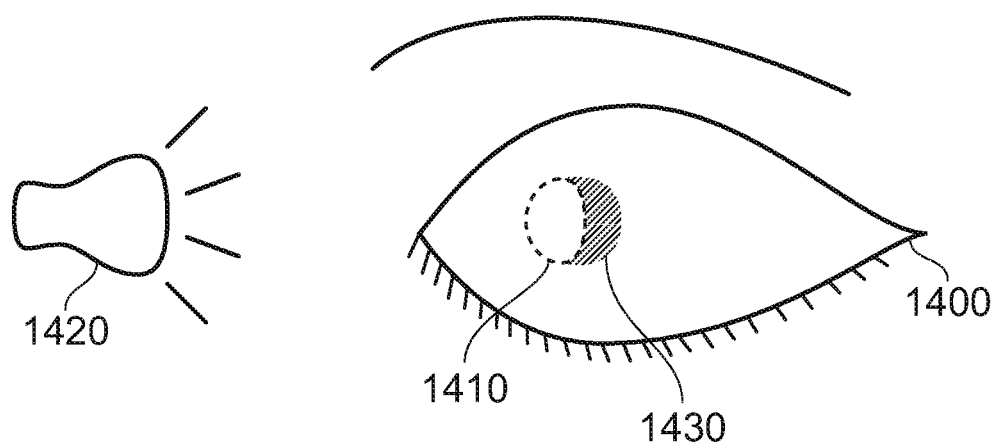
FIG. 14 schematically illustrates the generation of a shadow by the deformation.

Alternatively, or in addition, detection methods for the deformation may utilise shadows cast by the deformation of the user's eyelid by the cornea. In some embodiments, these shadows may be generated using a light source that is provided specifically for this purpose, while in others it may be sufficient that light from a display of an HMD or ambient light in the physical environment of the user is used to generate shadows. FIG. 14 schematically illustrates an example of an arrangement in which a light source is specifically supplied for the purpose of generating shadows that are cast by the deformation of the user's eye.

In FIG. 14, the user's eyelid 1400 is deformed by the cornea 1410. A light source 1420 is provided at an oblique angle to the user's eyelid 1400; the position illustrated in this Figure is entirely exemplary, and the light source 1420 may be located at any suitable position about the user's eye. The light emitted by the light source 1420 illuminates all (or at least a substantial portion) of the user's eyelid 1400, except for a shadowed area 1430. This shadow 1430 is caused by the light from the light source 1420 being obstructed by the deformation of the eyelid 1400 at the location of the cornea 1410.

The shadow 1430 may be detected by a camera arranged to be able to view the user's eyelid 1400; in particular, the size and shape of the shadow 1430 may be determined so as to identify the location of the cornea 1410. The shadow 1430 may be considered to be an example of a pattern, as discussed above.

In some embodiments, the light source 1420 emits light in the visible portion of the spectrum, while in other embodiments other wavelengths are used (such as IR). In some embodiments, the light source 1420 may be operated so as to emit light constantly, while in some embodiments the light source 1420 may be pulsed (for example, being switched on/off with a predetermined frequency in a strobe effect), or the light source 1420 may be activated in response to a detection of the user's eyes closing.

In some embodiments, two or more light sources may be provided; this can have the effect of generating multiple shadows. While each shadow may be more difficult to detect (as they may be fainter than if only a single light source were in use), having multiple shadows for reference may improve the accuracy or precision of the detection process.

Alternatively, or in addition, one or more of the light sources may be selectively activated in response to a last-known or predicted position of the user's eye. This can ensure that a light source with a suitably oblique angle may be selected as is appropriate for the expected location of the user's cornea, which may aid the accuracy of the eye-tracking arrangement.

Similarly a rapid alternation of two or more lights at different positions may be provided (e.g. using 1 light per video frame), with the corresponding shadow patterns being consistent with a given cornea position. Similarly, illumination using narrow band red, green and blue LEDs (or just two out of three) at different positions may provide different and complementary shadow images in the respective colour channels of a given video frame, again to assist with a calculation of the cornea position and hence gaze direction. Of course, any suitable wavelengths of light may be used; the use of red, green and blue is entirely exemplary.

Visible lights for the purposes of cornea detection may be activated after an image of the user's eye no-longer comprises a pupil (indicating that the user is no-longer able to see). Similarly these lights may be deactivated once the eyelid opens enough to reveal a part of the user's cornea (i.e. more than just the whites of the eye), as the pupil is likely to be revealed by the next video frame; it is preferable to deactivate visible lights before the user's pupil is revealed.

The detection of a shadow on the user's eyelid may be combined with a detection of a pattern as described with reference to FIGS. 12 and 13. This may be advantageous in generating more accurate results, or for identifying the location of the cornea in a method that may require less processing.

In one example, the detection of shadows may be simplified when they are cast onto a predetermined pattern. For example, if a chequerboard pattern (such as that of FIG. 12) were used then it would be apparent from a detection of darker squares where the shadow was present, and the size and shape of the shadow may be easier to determine against a uniform background with known reference points (such as the fact that the distribution and size of the squares in the pattern may be known).

In some embodiments, a separate determination of the size and/or location of the deformation of the user's eyelid may be performed using each of a pre-applied pattern on the user's eyelid and the shadow generated by a light source. The results of these determinations may be compared and/or combined to confirm or improve accuracy of the detection of the of user's eye position.

A number of modifications may be made to any of the embodiments described above that may result in a more efficient, accurate and/or precise detection of the user's eye position while the user's eye is closed. While some modifications may not directly improve accuracy, increases in efficiency of the detection processing may allow a more accurate/precise detection algorithm to be used without introducing a significant latency to the detection process. Several such modifications are discussed below; they may be utilised with any of the above embodiments and combined with each other as appropriate.

The human eye is capable of moving very quickly, and as the orientation of the eye may vary by a significant amount even during a period of time as short as a blink. However, there are limitations to the amount of the change in orientation in this period—such a limitation may be used to identify an area in which the user's cornea will be present. The detection process for identifying the location of the deformation of the user's eyelid may therefore be confined to this area, reducing the processing burden of the detection process. This is an example of physical limits of eye motion being used to predict a region of the eyelid in which the deformation may be detected.

Similarly, if a display associated with the eye-tracking arrangement is not fully immersive then there will be eye orientations that do not correspond to the viewer being focussed on a particular area of the display. For example, if the eye-tracking arrangement were being used with a television or computer display then there would be eye positions that would correspond to the user looking away from the displays. In such positions, no foveal rendering need be applied and therefore performing eye tracking of the closed eyes for these eye positions may be considered unnecessary. This may therefore further limit the area that is considered in the detection process, increasing efficiency.

In some embodiments, eye-tracking data captured when the eye is open and/or closing may be used to specify a most-likely area in which the user's cornea will be found. For example, if the user is changing their gaze direction towards the top of a display before blinking, it may be assumed that the motion will continue during the blink. The detection process may therefore be limited to the area in which the cornea would be expected to be in after this motion. This is an example of motion of the user's eye before the shutting is detected being used to predict a region of the eyelid in which the deformation may be detected.

Of course it may be possible that instead of limiting the area of the search, the detection processing is instead begun in the identified area (this may be applied to the above teachings, as well)—this may increase the efficiency of the detection without risking non-detection of the deformation due to being outside of the expected area.

Information about the content that is being displayed to a viewer may also be used to predict where a user is looking; for example, if a new character appears on screen or if a particular character is speaking then it may be assumed that the viewer would adjust their gaze so as to view this character. This means that an eye positon of the user may be predicted, and a most-likely region for cornea detection may be defined. This is an example of an analysis of image content being displayed to a user being used to predict a region of the eyelid in which the deformation may be detected.

Use data may also be recorded that may assist the eye-tracking arrangement in increasing the efficiency of the detection process. For example, if a user's eyes often move in a particular direction or by a particular amount when blinking, then the area in which the deformation of the user's eyelid would be expected to be detected could be reduced. Measurements of a maximum movement speed, patterns of eye motion, and identification of displayed content that are of particular interest to a user are all examples of information that may be gathered to assist with the eye-tracking process.

It has been observed that during blinks, the eyes may rotate as part of an automatic motion associated with the blink. Such motion may be factored into any predictions, for example, as this may influence predictions of what orientation the user's eye will have when the blink ends.

In many of the described arrangements it may be beneficial to perform a calibration process so as to increase the accuracy of the detection. Such a process may comprise asking users a series of questions relating to their vision—such as whether they use contact lenses, usually wear glasses, or otherwise have any defects in their vision that could cause incorrect results to be derived for the detection. The process may further comprise recording a user performing a series of predetermined eye motions (with the eyes open or closed) while being tracked so as to generate a data set upon which further tracking may be based. The accuracy of the eye-tracking process may be affected by a number of factors unique to a user, such as the thickness of their cornea and/or eyelid, the wearing of glasses and/or use of heavy makeup or the like, and so calibration data may assist with overcoming these challenges.

The calibration data may further be used to determine an expected accuracy of the method. For example, it may be determined that the eye position can be located to within X millimetres; in response to this, the size of one or more of the regions that are used in the foveal rendering process may be varied appropriately so as to ensure that even if there is a slight error a suitable image will be generated. This size may be used for a number of frames during the blink and/or immediately following the blink, or the size may be used for the display of the entirety of the video content.

Having a rendering region that is proportional to the determined accuracy of the eye-tracking process when the eye is closed is advantageous over earlier arrangements in which a larger area (such as the whole of the image) is rendered with high-resolution, as this method only requires the high-resolution area to be as large as the uncertainty in the tracking process rather than being large enough so as to cover every possible movement of the eye during the blink. This in turn enables the more general use of a higher-resolution HMD, in which the data rate for a full-screen high resolution image would be more than a source device, transmission scheme and/or HMD could otherwise handle.

Figure 15:
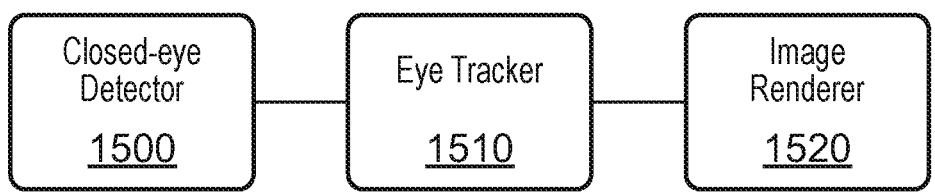
FIG. 15 schematically illustrates an eye-tracking and image rendering system.

FIG. 15 schematically illustrates an eye-tracking and image rendering system. This system comprises a closed-eye detector 1500, an eye tracker 1510 and an image renderer 1520.

The closed-eye detector 1500 is operable to detect when a user has closed one or more of their eyes. This may be performed in any suitable way; for example, a standard eye-tracking system could be used as a closed-eye detector—a failure to track the pupils of a user would be indicative of eyes closing. In some embodiments, a simple detector that is operable to determine the reflectivity of the surface may be used—a user's eyelid will provide a different reflection to that of the user's eye. It may be possible to connect electrodes or the like to a user's face in order to detect the motion of muscles associated with opening and closing the user's eyes.

The eye tracker 1510 is operable to detect an eye orientation in dependence upon a measured deformation of an eyelid corresponding to an eye that has been detected to be shut. The configuration of an exemplary eye tracker 1510 is described below with reference to FIG. 16.

The image renderer 1520 is operable to render a foveated image for display in response to the detected eye orientation. In some embodiments, the rendered image has a higher-resolution portion, as discussed with reference to FIGS. 10A and 10B. In some of these embodiments, the size of the higher-resolution portion is dependent upon a determined accuracy of the detection of the eye orientation.

Each of these units may be located at an HMD or other head-mountable device that is to be worn by a user, or they may be located in separate devices entirely. For example, the image renderer 1520 may be located instead at a processing device, such as a games console, that is operable to communicate with the eye tracker 1510 and/or the closed-eye detector 1500.

Figure 16:
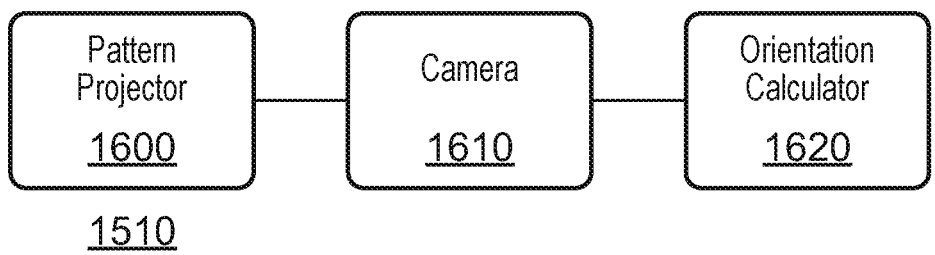
FIG. 16 schematically illustrates an eye tracker.

FIG. 16 schematically illustrates an eye tracker 1510. This example of an eye tracker comprises a pattern projector 1600, a camera 1610 and an orientation calculator 1620, although in some embodiments additional or alternative components may be used to form the eye tracker 1510.

The pattern projector 1600 is operable to generate a pattern on the user's eyelid. As noted above, this pattern may be generated using structured light projected onto the user's eyelid, or the pattern may be a shadow cast by the deformation of the user's eyelid (in which case the pattern projector may be one or more light sources each arranged to illuminate the user's eyelid from an oblique angle).

Of course, the pattern projector 1600 may be omitted in embodiments in which the pattern is affixed to the user's eyelid; as discussed above, this may be achieved using make-up or temporary tattoos or the like. Additionally, the pattern projector 1600 may be omitted when there is no pattern used at all; while a pattern may assist in generating an accurate detection, it is not essential for doing so.

As discussed above, in some embodiments combinations of the above implementations may be used—for example, using both patterns (projected or otherwise) in conjunction with shadows.

The camera 1610 may be any suitable imaging device for determining a deformation of the user's eyelid. In some embodiments, this may be a depth detector or depth camera, while in other embodiments RGB or IR cameras or the like may be used. The camera 1610 should be arranged so as to be able to capture images of the user's eyelid, and in particular regions of the eyelid comprising a pattern.

The orientation calculator 1620 is operable to use the images and information captured by the camera 1610 to identify any deformation of the user's eyelid, and to use information about the deformation to derive information about the orientation of the user's eye. In some embodiments, this may comprise the comparison of captured images of patterns on the user's eyelid with reference images of the pattern. In some embodiments, this may comprise the detection of shadows within an image that are indicative of a deformation of the user's eyelid as a result of the presence of the cornea.

Figure 17:
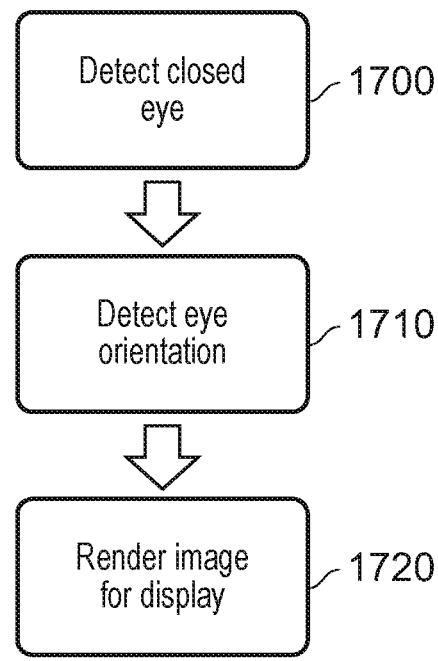
FIG. 17 schematically illustrates an eye-tracking and image rendering method.

FIG. 17 schematically illustrates an eye-tracking and image rendering method for tracking one or more of a user's eyes and rendering content in dependence upon the eye-tracking.

A step 1700 comprises detecting when a user has closed one or more of their eyes.

A step 1710 comprises detecting an eye orientation in dependence upon a measured deformation of an eyelid corresponding to an eye that has been detected to be shut.

A step 1720 comprises rendering a foveated image for display in response to the detected eye orientation, for example using foveal rendering techniques.

Figure 18:
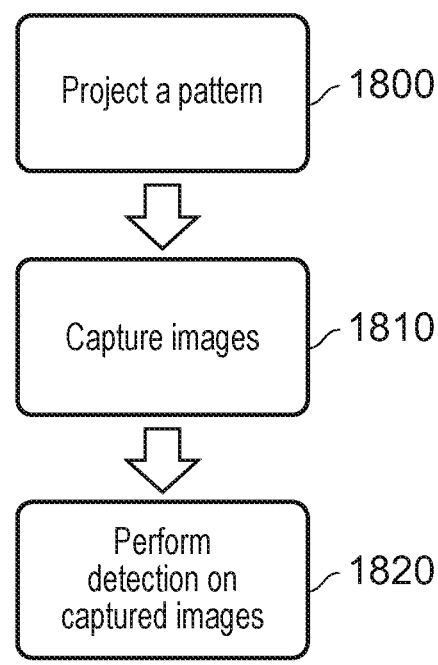
FIG. 18 schematically illustrates a method for detecting eye orientation.

FIG. 18 schematically illustrates a method for detecting eye orientation, for example corresponding to step 1710 of the method of FIG. 17.

A step 1800 comprises projecting a pattern onto the eyelid of a user, for example using structured light or by illuminating the eyelid from an oblique angle so as to generate shadows. Of course, this step may be omitted in embodiments in which A step 1810 comprises capturing images of the user's eyelids, and in particular images of any patterns that are projected or otherwise affixed to the user's eyelids.

A step 1820 comprises performing a detection on captured images so as to detect deformations of the user's eyelids corresponding to the position of the user's cornea and in turn detect the user's eye orientation in dependence upon the detected deformation.

The techniques described above may be implemented in hardware, software or combinations of the two. In the case that a software-controlled data processing apparatus is employed to implement one or more features of the embodiments, it will be appreciated that such software, and a storage or transmission medium such as a non-transitory machine-readable storage medium by which such software is provided, are also considered as embodiments of the disclosure.

The invention claimed is:

1. An eye tracking system for tracking one or more of a user's eyes, the system comprising:
   an closed-eye detector operable to detect when a user has closed one or more of their eyes;
   an eye tracker operable to detect an eye orientation in dependence upon a measured deformation of an eyelid corresponding to the an eye that has been detected to be shut; and
   an image renderer operable to render a foveated image for display in response to the detected eye orientation.

2. A system according to claim 1, wherein the deformation of the eyelid is measured using a depth detector.

3. A system according to claim 1, wherein the deformation of the eyelid is detected by identifying a deformation of a pattern on the user's eyelid.

4. A system according to claim 3, wherein the pattern is a generated using structured light projected onto the user's eyelid.

5. A system according to claim 3, wherein the pattern is affixed to the user's eyelid.

6. A system according to claim 3, wherein the pattern is a shadow cast by the deformation of the user's eyelid.

7. A system according to claim 6, wherein the shadow is generated by light illuminating the user's eyelid from an oblique angle.

8. A system according to claim 7, comprising one or more light sources each arranged to illuminate the user's eyelid from an oblique angle.

9. A system according to claim 1, wherein physical limits of eye motion are used to predict a region of the eyelid in which the deformation may be detected.

10. A system according to claim 1, wherein motion of the user's eye before the shutting is detected is used to predict a region of the eyelid in which the deformation may be detected.

11. A system according to claim 1, wherein analysis of image content being displayed to a user is used to predict a region of the eyelid in which the deformation may be detected.

12. A system according to claim 1, wherein the size of the higher-resolution portion of the foveated image is dependent upon a determined accuracy of the detection of the eye orientation.

13. An eye tracking method for tracking one or more of a user's eyes, the method comprising:
   detecting when a user has closed one or more of their eyes;
   detecting an eye orientation in dependence upon a measured deformation of an eyelid corresponding to an eye that has been detected to be shut; and
   rendering a foveated image for display in response to the detected eye orientation.

14. A machine-readable non-transitory storage medium which stores computer software, which when executed by a computer system, causes the computer system to perform an eye tracking method for tracking one or more of a user's eyes, by carrying out actions, comprising:
   detecting when a user has closed one or more of their eyes;
   detecting an eye orientation in dependence upon a measured deformation of an eyelid corresponding to an eye that has been detected to be shut; and
   rendering a foveated image for display in response to the detected eye orientation.

* * * * *